United States Patent [19]

Burton

[11] Patent Number: 4,474,917
[45] Date of Patent: Oct. 2, 1984

[54] PHENOLIC PHOSPHITE ANTIOXIDANT FOR POLYMERS

[75] Inventor: Lester P. J. Burton, Pleasant Ridge, Mich.

[73] Assignee: Ethyl Corporation, Richmond, Va.

[21] Appl. No.: 382,629

[22] Filed: May 27, 1982

Related U.S. Application Data

[63] Continuation-in-part of Ser. No. 350,085, Feb. 18, 1982.

[51] Int. Cl.$^3$ .................... C07F 9/145; C07F 9/146
[52] U.S. Cl. .................................. 524/152; 260/930; 260/953; 524/101; 524/128; 252/49.8
[58] Field of Search ............... 524/128, 152, 342, 291; 260/930, 973, 976, 953, 952, 967, 942; 568/720, 722; 252/49.8

[56] References Cited

U.S. PATENT DOCUMENTS

| | | | |
|---|---|---|---|
| 3,026,264 | 3/1962 | Rocklin et al. | 524/342 |
| 3,039,993 | 6/1962 | Friedman | 260/45.8 |
| 3,053,803 | 9/1962 | Jaffe et al. | 524/342 |
| 3,285,855 | 11/1966 | Dexter et al. | 524/291 |
| 3,297,631 | 1/1967 | Bown et al. | 260/45.95 |
| 3,458,473 | 7/1969 | Starnes | 524/342 |
| 3,493,638 | 2/1970 | Meltsner | 260/953 |
| 3,567,863 | 3/1971 | Spacht | 524/152 |
| 3,635,884 | 1/1972 | Meltsner | 260/45.85 |
| 3,949,024 | 6/1976 | Beck et al. | 260/953 |
| 4,187,212 | 2/1980 | Zinke et al. | 260/45.8 |
| 4,233,207 | 11/1980 | Spivack | 260/45.7 |
| 4,246,170 | 1/1981 | Evans | 524/128 |
| 4,257,927 | 3/1981 | Leistner et al. | 524/128 |
| 4,282,141 | 8/1981 | Minagawa et al. | 260/45.7 |
| 4,321,218 | 3/1982 | Rasberger et al. | 260/967 |

OTHER PUBLICATIONS

C. David Gutsche et al., "Calixarenes 4, The Synthesis, Characterization and Properties of the Calixarenes from p-tert-Butylphenol"-J. Am. Chem. Soc., 1981, 103, 3782-3792.

Primary Examiner—V. P. Hoke
Attorney, Agent, or Firm—Donald L. Johnson; John F. Sieberth; John F. Hunt

[57] ABSTRACT

Phenolic-phosphite antioxidants for use alone in polyolefins or in admixture with synergists, phenolic/-phosphite antioxidants, and the like. The adduct formed by reacting a phosphorus trihalide, preferably PCl$_3$, with 1,3,5-trimethyl-2,4,6-tris(3',5'-di-tert-butyl-4'-hydroxybenzyl)benzene, e.g., is useful for antioxidant activity in organic materials. Various other phenolic adducts also show antioxidant activity. The adducts are formed by reacting PCl$_3$, e.g., with a large phenolic compound having three or more phenolic moieties. The adducts contain components which are noncyclic with respect to phosphite moieties.

6 Claims, No Drawings

PHENOLIC PHOSPHITE ANTIOXIDANT FOR POLYMERS

CROSS REFERENCE TO RELATED APPLICATION

This application is a continuation-in-part of application Ser. No. 350,085, filed Feb. 18, 1982.

BACKGROUND OF THE INVENTION

I. Field of the Invention

This invention relates in general to antioxidants, and antioxidant synergists for organic materials and in particular to a process for making a phenolic phosphite by reacting a phosphorus trihalide, e.g. PCl₃, and large phenolics such as 1,3,5-trimethyl-2,4,6-tris(3,5-di-tert-butyl-4-hydroxybenzyl) benzene as well as the adducts made thereby.

II. Description of the Prior Art

Phosphites are used in organic polymers and other organic substrates as high temperature antioxidants. The phosphites are generally considered better than phenolic antioxidants at high temperatures because they eliminate hydroperoxides which decompose and lead to autooxidation chain reactions. Thus phosphites are important for processing stability during polyolefin extrusion and during other operations with organic substrates.

Various phosphites are well known in the art such as the aryl phosphite shown in U.S. Pat. No. 4,282,141 to Minagawa et al, and the phenyl phosphonites disclosed in U.S. Pat. No. 4,233,207 to Spivack.

Phenolic and phosphite antioxidants are often used together in polyolefin homopolymers and copolymers to provide antioxidant protection for both low and high temperature exposure. Unfortunately additional expense is encountered as more additives in larger amounts are needed for a polymer. Thus there exists a need for effective antioxidants at a reasonable additive price, not only for polyolefins but other substrates as well.

Other phosphite antioxidants are those disclosed in U.S. Pat. No. 4,187,212 to Zinke et al, and U.S. Pat. No. 3,039,993 to Friedman.

Various alkylated phenolics are well known in the art such as those disclosed in U.S. Pat. No. 3,026,264. The high temperatures referred to above with regard to phosphites, are high enough to affect the rigidity of a polyolefin, but are generally below the point where the polyolefin would immediately decompose or ignite.

SUMMARY OF THE INVENTION

According to the present invention, a phosphorus trihalide is reacted with 1,3,5-trimethyl-2,4,6-tris(3,5-di-tert-butyl-4-hydroxybenzyl) benzene to form an adduct. The adduct is known to have about five major components. The adduct is also known to have about 0.1 to 9.0 weight percent phosphorus and about 0.0 to 5.0 weight percent chlorine. Thus the invention is a process for making the adduct, the adduct per se, compositions including the adduct, and methods of using the adduct to protect an organic material.

Also according to the invention, a phosphorus trihalide is reacted with tetrakis(methylene-3[3',5'-di-tert-butyl-4'-hydroxyphenyl]propionate) methane; 2,4,6-tris(3,5-di-tert-butyl-4-hydroxybenzyl)phenol; the o-tert-butylphenol/formaldehyde reaction product reacted with formaldehyde and a mixture of 2,6-di-tert-butylphenol, 4,4'-methylenebis(2,6-di-tert-butylphenol), and 3,5-di-tert-butyl-4-hydroxybenzyl alcohol, such mixture being the heel from production of the 3,5-di-tert-butyl-4-hydroxybenzyl alcohol; and other large phenolics. The large phenolics are those that form oligomers with PCl₃ rather than monomers or small ring phosphites such as is done with pentaerythritol or compounds having the diphenolic structure:

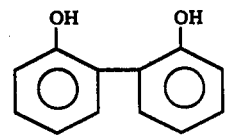

Thus the adducts of the invention form polyphenolic phosphites with —P—O— linkages between a short series of aromatic rings. The large phenolics have three or more phenolic moieties. The adducts have noncyclic phosphite moieties.

The process for making the adduct comprises reacting a phosphorus trihalide such as PCl₃, PF₃, or PBr₃ with the substituted tris phenol compound I:

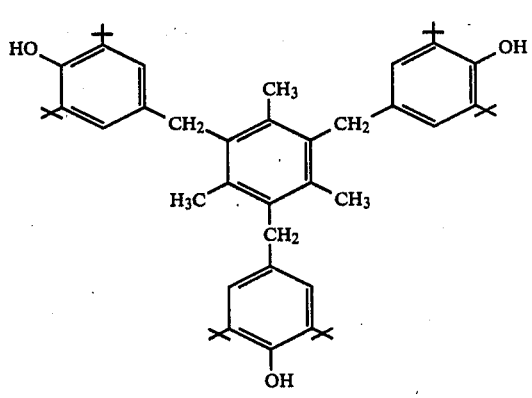

A phosphorus trihalide may also be reacted with any of the phenolic compounds mentioned above such as:

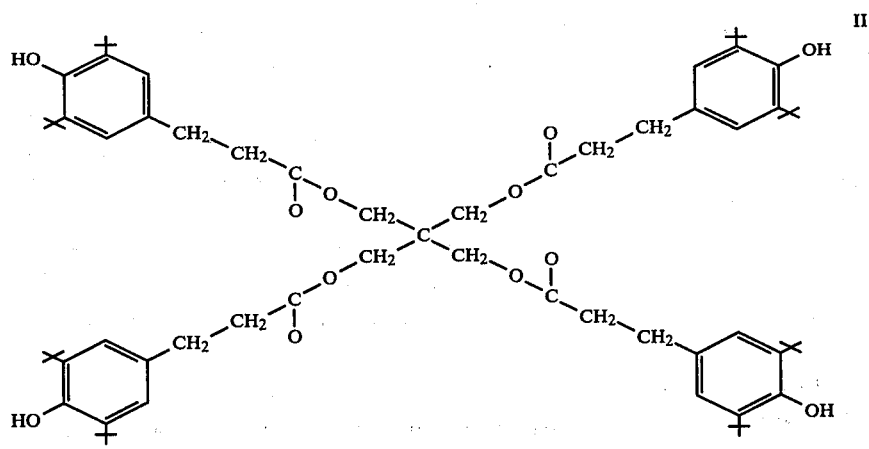
II
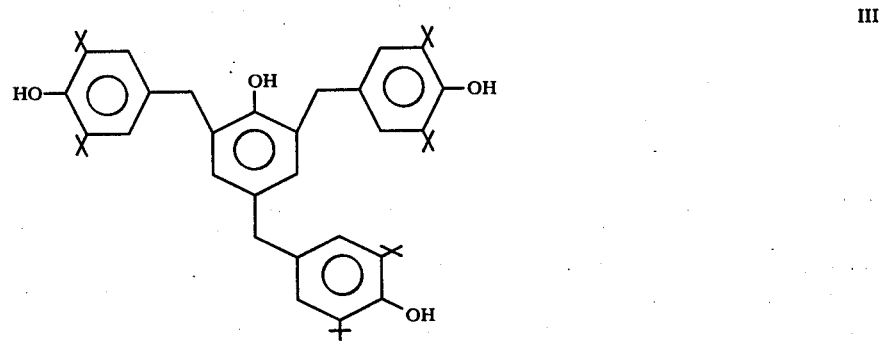
III
Although Applicant has not yet successfully produced an adduct of the invention from the following commercial phenolics, they appear to be suitable for the invention:
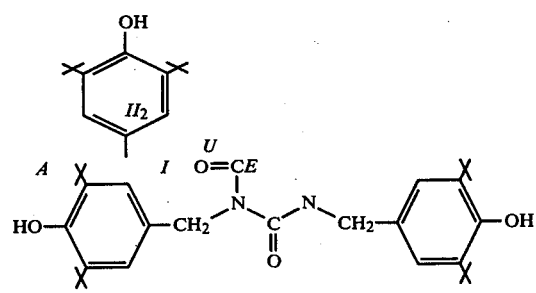
1,3,5-tris-(3,5-di-tert-butyl-4-hydroxybenzyl)isocyanurate -continued

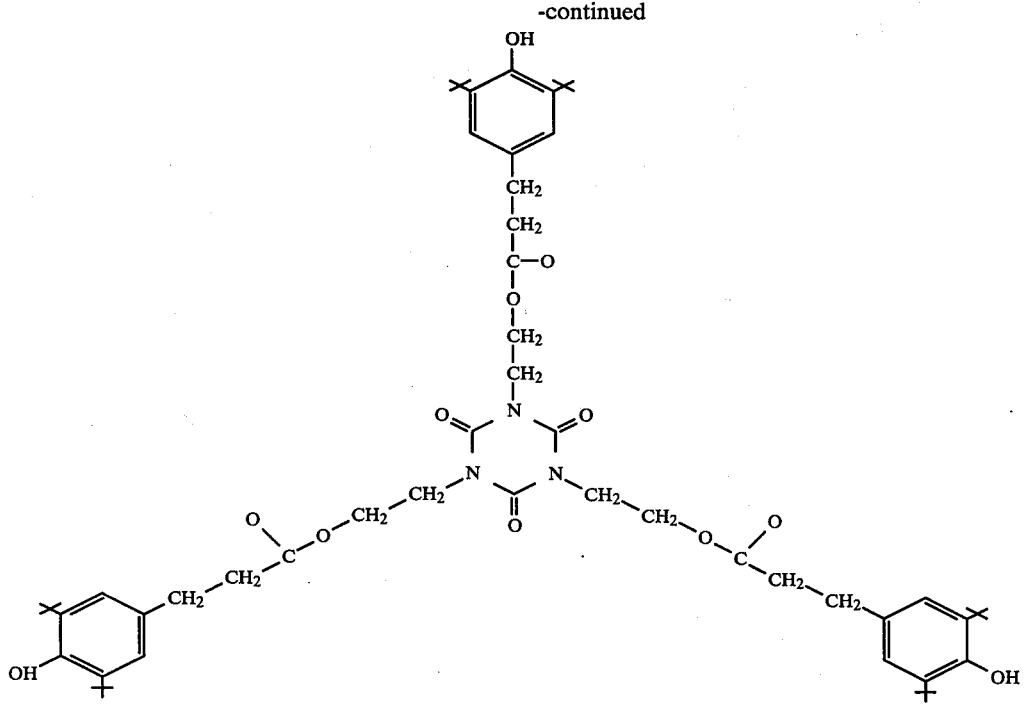

3,5-Di-tert-butyl-4-hydroxyhydrocinnamic acid triester with 1,3,5-tris(2-hydroxyethyl)-s-triazine-2,4,6(1H,3H,5H)-trione The above phenolics are available from B. F. Goodrich Chemical Company as Goodrite®3114 and 3125 phenolic antioxidants, respectively.

The reaction is preferably carried out by heating about 0.1 to 3.0 mole parts phosphorus trihalide with each mole part of the phenolic compound. The compound I is available from Ethyl Corporation as Ethanox®330 phenolic antioxidant. Reaction temperatures suitable for the reaction fall within the range of 20° to 70° C. at normal pressure but this range may vary somewhat for subatmospheric or superatmospheric reaction pressures or higher boiling solvents which are also suitable for the reaction.

The most preferred phosphorus trihalide for making the novel adduct is $PCl_3$ since the adducts made with $PCl_3$ have shown not only superior antioxidant activity but synergistic activity as well.

The adducts made by the process of this invention protect substrate polyolefins, for example, in a manner previously achieved only by the addition of both a phenolic antioxidant and a phosphite compound. Moreover, the protection is in some cases superior to such combination-protected polyolefins.

The adducts of the present invention are known to contain at least one component (of several) which has at least one P—O bond. Thus the phosphorus from $PX_3$ is likely linked to the compound I structure at the oxygen atom from one of the three available hydroxy groups. The adducts of the invention combine the advantages of both a phenolic and a phosphite antioxidant.

Furthermore, the adducts formed by the process of the invention have shown synergy with other antioxidants in polyolefins. Another useful synergist for the adduct of the invention is distearyl thiodipropionate (DSTDP). Also suggested is the dilauryl analog DLTDP.

Also according to the present invention, stabilized organic compositions are provided which contain an antioxidant amount of a novel adduct. The adducts contain components which are new compounds.

The invention is, therefore, a process for making a phenolic phosphite adduct, said process comprising reacting a phosphorus trihalide with 1,3,5-trimethyl-2,4,6-tris(3,5-di-tert-butyl-4-hydroxybenzyl)benzene to form an adduct of the two reactants.

The invention is also a process for making a phenolic phosphite adduct by reacting a phosphorus trihalide with a calix [n] arene where n≧4 or another large phenolic compound with at least three phenolic moieties such as compound II or III to form an adduct having an oligomeric phenolic phosphite component.

The invention also includes the isolated adducts of the above reactions.

The invention also includes organic material normally susceptible to gradual oxidative degradation, containing an antioxidant amount of an adduct formed by reacting a phosphorus trihalide with 1,3,5-trimethyl-2,4,6-tris(3,5-di-tert-butyl-4-hydroxybenzyl)benzene or another large phenolic such as compounds II and III.

The invention also includes a method for protecting an organic material normally susceptible to gradual degradation in the presence of oxygen, said method comprising adding to said polyolefin an antioxidant amount of an adduct formed by reacting a phosphorus trihalide with 1,3,5-trimethyl-2,4,6-tris(3,5-di-tert-butyl-4-hydroxybenzyl)benzene or another large phenolic such as compounds II and III. The adducts are intimately mixed with substrate by any known means.

Finally, the invention also includes compositions of the adducts of reaction in combination with a specific polyolefin, an antioxidant, or both.

It is therefore an object of the invention to provide a process for making an adduct of a large phenolic compound and a phosphorus trihalide.

It is also an object of the present invention to provide an adduct which shows synergism with other phenolics, phosphites, and sulfur compounds such as the dilauryl and distearyl thiodipropionates.

It is also an object of the invention to protect a polyolefin with an adduct of a phosphorus trihalide and a large phenolic compound either alone or with another additive.

These and other objects of the present invention will be better understood by a reading of the following detailed description.

DESCRIPTION OF THE PREFERRED EMBODIMENTS

A preferred embodiment of the invention is a reaction of a phosphorus trihalide with compound I. A preferred embodiment is also a composition of organic material and an antioxidant portion of an adduct of the invention.

According to a preferred embodiment of the invention, the compound I is reacted with a phosphorus trihalide by heating for an extensive time such as 24 hours. It is noted that the adduct appears to be formed in a much shorter time (less than one hour) but the heating may be continued for thoroughness.

The $PX_3$ and compound I are preferably reacted by first forming an alkali metal salt such as the sodium salt of compound I in a solvent before refluxing with $PX_3$. Preferably the $PX_3$ is also dissolved in a small portion of the same or a compatible solvent. Also the reaction mixture may be cooled, washed with alcohol, and chemically dried to improve color characteristics.

It is contemplated that the adducts of $PX_3$ and phenolic compounds will most advantageously be used with a thioester, but may be used alone. It may also be more beneficial in certain polyolefins or other organic substrates and for certain purposes to use the adduct in admixture with a phenolic antioxidant, whether preblended or separately incorporated into an organic substrate.

Similarly, a preferred embodiment of the invention is made in the same manner as for compound I, but with a calix [n] arene or other large phenolic with three or more phenolic moieties such as compound II or III so as to form a polyphenolic phosphite.

The antioxidant adducts of the present invention can be used in a broad range of organic material normally subject to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but rather, the gradual deterioration of the organic composition due to the effects of oxygen over an extended period of time.

The adducts of the present invention contain components incorporating the structure of the respective large phenolic such as compound I and should be usable with the broad array of organic materials for which large phenolics such as compound I are used. Those organic materials include plastics, resins, rubber, and waxes. The adducts of the invention are highly effective stabilizers with generally low volatility.

The antioxidant phenolic phosphites of the present invention are especially important for protecting organic substrates during processing where the substrates are subjected to thermal and physical stress. The organic materials protected are often kneaded, extruded, or milled at temperature high enough to make the material molten.

Examples of organic materials in which the additives may be useful include polymers, both homopolymers and copolymers, of olefinically unsaturated monomers, for example, polyolefins such as polyethylene, polypropylene, polybutadiene, polybutylene, low density polyethylene, linear low density polyethylene (often made from the primary monomer ethylene and about 5–10% comonomer) and the like.

Also, poly-halohydrocarbons such as polyvinyl chloride, polychloroprene, polyvinylidene chloride, polyfluoro olefins, and the like may be afforded stabilization. The additives may be used to provide antioxidant protection in natural and synthetic rubbers such as copolymers of olefinically unsaturated monomers including styrene-butadiene rubber (SBR rubber), ethylene-propylene copolymers, ethylene-propylenediene terpolymers such as the terpolymer of ethylene, propylene and cyclopentadiene or 1,4-polybutadiene rubber may be protected. Poly-2-chloro-1,3-butadiene (neoprene) and poly-2-methyl-1,3-butadiene (isoprene rubber) may be stabilized by the present additives. Likewise, acrylonitrile-butadiene-styrene (ABS) resins are effectively stabilized. Ethylenevinyl acetate copolymers may be protected, as may be butene-methylacrylate copolymers. Nitrogen-containing polymers such as polyurethanes, nitrile rubber, and lauryl acrylate-vinyl-pyrrolidone copolymers may be effectively stabilized. Adhesive compositions such as solutions of polychloroprene (neoprene) in toluene may be protected.

Petroleum oils such as solvent-refined, hydrocracked, midcontinent lubricating oil and Gulfcoast lubricating oils may be effectively stabilized. In hydrocarbon lubricating oils, both mineral and synthetic, the present additives may be particularly effective when used in combination with a zinc-dihydrocarbyldithiophosphate, e.g. zinc dialkyldithiophosphate or zinc dialkaryldithiophosphate.

Synthetic ester lubricants such as those used in turbines and turbojet engines may be given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate may be effectively protected. Heavy petroleum fractions such as tar and asphalt may also be protected should the need arise.

Polyamides such as adipic acid-1,6-diaminohexane condensates and poly-6-aminohexanoic acid (nylon) may be effectively stabilized. Polyalkylene oxides such as copolymers of phenol with ethylene oxide or propylene oxide may be stabilized. Polyphenyl ethers such as poly-2,6-dimethylphenyl ether formed by polymerization of 2,6-dimethylphenol using a copper-pyridine catalyst may be stabilized. Polycarbonate plastics and other polyformaldehydes may also be protected.

Linear polyesters such as phthalic anhydride-glycol condensates may be given a high degree of protection. Other polyesters such as trimellitic acid-glycerol condensates may also be protected. Polyacrylates such as polymethylacrylate and polymethylmethacrylate may be effectively stabilized. Polyacrylonitriles and copolymers of acrylonitriles with other olefinically unsaturated monomers such as methylmethacrylates may also be effectively stabilized.

The adducts of the invention may be used to protect any of the many organic substrates to which an antioxidant is normally added. The adducts can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethyl-silicone lubricants, phosphate lubricants such as tricresyl-phosphate, and the like.

The adduct may be incorporated into the organic substrate in a small but effective amount so as to provide the required antioxidant protection. A useful range is from about 0.01 to about 0.5 weight percent, and a preferred range is from about 0.05 to 0.3 weight percent.

Methods of incorporating the adduct into the substrate are well known. For example, if the substrate is liquid the adduct can be merely mixed into the substrate. Frequently the organic substrate is in solution and the adduct is added to the solution and solvent removed. Solid organic substrates can be merely sprayed with a solution of the adduct in a volatile solvent. For example, stabilized grain products might be made by spraying the grain with a toluene solution of the adduct. In the case of rubbery polymers the adduct may be added following the polymerization stage by mixing it with the final emulsion or solution polymerization mixture and then coagulating or removing solvent to recover the stabilized polymer. It can also be added at the compounding stage by merely mixing the adduct with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The following examples serve to explain the invention in the best mode now known to me.

EXAMPLE 1

The adduct of the invention was prepared in two steps, first forming the sodium salt of 1,3,5-trimethyl-2,4,6-tris(3,5-di-tert-butyl-4-hydroxybenzyl)benzene (compound I) and then reacting phosphorus trichloride with the heated sodium salt of compound I.

Tetrahydrofuran (THF, 50 ml) was dried over Na/benzophenone. A 0.021 mole (0.52 g) portion of 98 percent NaH and a 0.02 mole (15.5 g) portion of compound I were cautiously combined with the THF in a round bottom flask equipped with a stirrer and addition funnel. The mixture effervesced briefly and formed a slurry which was brought to reflux for one hour.

A solution of 0.07 mole (0.6 ml) $PCl_3$ in 10 ml dry THF was added dropwise to the refluxing slurry and then allowed to reflux for 22 hours (although reaction appeared complete in only a short period). The reaction mixture was cooled, poured over 150 ml ethylacetate to hold the organics, then washed twice with a total of 200 ml 50% saturated NaCl aqueous solution to remove aqueous solubles including NaCl, and finally dried over anhydrous $Na_2SO_4$ after removing the aqueous layer in a separating funnel. A pale yellow solid (16.7 g) with a melting point of 130°–140° C. was recovered. The acid number of the product both before and after boiling in water for 20 minutes was 0.0.

Further analyses showed the presence of five major components one of which appeared as compound I in a thin layer chromatography comparison. About 51% compound I remained in the adduct. The adduct contained 0.93 weight percent phosphorus and 1.77 weight percent chlorine. Washing the adduct with ethanol yields a white solid with only 1.5 weight percent phosphorus. Both the initially produced yellow adduct and the ethanol-washed white product were subsequently used in a polyolefin or other organic material.

Most commercial antioxidants have a high amount of phosphorus. For example compare distearyl pentaerythritol diphosphite at 7.2–7.8 weight percent phosphorus. Nevertheless, good results have been realized with the adduct of Example 1.

EXAMPLE 1A

The above experiment was repeated to prove reproducibility. The analyses of the adducts are compared in Table 2.

EXAMPLE 2

The initial yellow adduct made in Example 1 (before ethanol wash), 0.02 g and about 0.05 g distearyl thiodipropionate (DSTDP) were dissolved in a few drops of methylene chloride and mixed in a blender. The solution was poured into about 20 g Norchem's Profax-6500 ™ polypropylene (in powder form). Thereafter the stabilized polypropylene was compression molded at 400° F. in a Pasadena Hydraulic Press into several one inch by one-half inch plaques of about 2.5 mils thickness. The plaques were thereafter placed in an air circulating oven set at 150° C. and periodically checked for cracks or other signs of degradation caused by the oven aging.

EXAMPLES 3–4

Other plaques were similarly prepared so as to provide polypropylene with about 0.1 and 0.3 weight percent compound I only (without DSTDP). For comparison, an unprotected polypropylene plaque develops cracks and completely degrades within about four hours. Polypropylene protected with 1,3,5-trimethyl-2,4,6-tris(3,5-di-tert-butyl-4-hydroxybenzyl)benzene (compound I) alone at about 0.3 weight percent fails at about 600 hours. Polypropylene protected with a small portion of compound I plus a phosphite antioxidant such as distearyl thiodipropionate (DSTDP) fails at about 1000 hours.

EXAMPLE 5

Several plaques were prepared from the alcohol-washed white adduct of Example 1 in precisely the same manner and consistency as Example 2.

The oven aging results for Examples 2–5 are summarized in Table 1 below:

TABLE 1

150° C. Polypropylene Oven Aging

| Ex. No. | Wt. % Adduct | Wt. % DSTDP | Hours to Fail |
|---|---|---|---|
| 2 | 0.10 | 0.25 | 2712 |
| 3 | 0.10 | — | 936 |
| 4 | 0.30 | — | 2064 |
| 5 | 0.10 | 0.25 | 2187 |
| Compound I alone at 0.3% | | | 600 (typical) |
| Compound I at 0.10% plus 0.25% DSTDP | | | 1000 (typical) |

Thus the adduct of the invention performed better at 0.1 weight percent (Example 3) than did phenolic antioxidant compound I at about 0.3 weight percent. Also the results of Example 2 shows the unexpected synergistic improvement of the adduct with a thioester, DSTDP over a phenolic antioxidant plus DSTDP.

EXAMPLE 6

The same general procedure was followed as for Example 1 except that the ratio of phenolic compound I to $PCl_3$ was lowered from 3:1 to 2:1 in order to raise the phosphorus content and lower the amount of unreacted starting material. Also, less NaCl was used to break up the emulsion in the aqueous work-up so as to minimize the chlorine content.

A solution of 0.059 mole (46 g) phenolic compound I and 0.012 mole (3 g) 95% NaH in 150 ml. dry THF (distilled from Na/benzophenone) was heated at reflux for one and one-half hours. A solution of 0.028 mole (2.4 ml.) $PCl_3$ in 6 ml. THF was added to the hot solution under nitrogen over a period of one-half hour. The reaction mixture was thereafter maintained at reflux for 20 hours.

The reaction mixture was cooled, poured over 200 ml. ethyl acetate, washed with 100 ml. water, and washed with 100 ml. water containing a small amount of NaCl to break up the emulsion. The organic layer was dried over $Na_2SO_4$ and concentrated under vacuum. The yield was 46.5 g pale yellow adduct having the analysis given in Table 2.

EXAMPLE 7

The same general procedure was followed as for Example 6 except that pyridine was used as an HCl scavenger.

A solution of 0.025 mole (2.2 ml., 3.4 g) $PCl_3$ in 10 ml. dry THF was added to a solution of 0.05 mole (38.8 g) compound I, 0.05 mole (4 ml.) pyridine, and 90 ml. dry THF, under nitrogen over a period of only five minutes. The resulting slurry was heated to reflux for 14 hours. The reaction mixture was cooled in an ice bath and filtered to remove pyridine.HCl.

The filtrate was concentrated under vacuum to a thick yellow oil. The oil was dissolved in 100 ml. ethyl acetate and washed with three 100 ml. portions of water, then 80 ml. saturated $NaHCO_3$. The organics were dried over $Na_2SO_4$ and concentrated under vacuum to yield 38.5 g pale yellow solid. The analysis is given in Table 2 below.

TABLE 2

| Example | Wt. % P | Wt. % Cl | Wt. % Na | P:Cl* | % Compound # |
|---|---|---|---|---|---|
| 1 | 0.93 | 1.8 | 0.64 | 1:0.8 | 51 (I) |
| 1 EtOH (after wash) | 1.5 | 2.4 | 0.88 | 1:0.6 | 49 (I) |
| 1A | 1.0 | 3.8 | 2.3 | 1:0.2 | 42 (I) |
| 6 | 1.3 | 1.1 | 0.1 | 1:0.8 | 43 (I) |
| 7 | 1.7 | 0.0 | 0.0 | — | 55 (I) |
| 9 | 2.5 | 2.0 | 0.05 | 1:0.7 | — |
| 10 | 1.1 | 0.8 | 0.3 | 1:0.3 | 46 (II) |
| 11 | 2.8 | 0.24 | 0.9 | — | 8 (III) |
| 12 | 1.9 | 0.24 | — | — | — |

*mole ratio after subtracting Cl attributed to NaCl

Additional oven aging tests were carried out as above in Table 1 for plaques prepared from another sample of Norchem's Profax-6501 ™ polypropylene.

TABLE 3

150° C. Polypropylene Oven Aging

| Sample | Wt. % Adduct | DSTDP | Hours to Fail |
|---|---|---|---|
| Example 1A | 0.1 | | 312 |
| 1A | 0.3 | | 1032 |
| 1A | 0.1 | 0.25 | 1584 |
| 2-4 | 0.1 | | 240 |
| 2-4 | 0.3 | | 1488 |
| 2-4 | 0.1 | 0.25 | 1656 |
| 5 | 0.1 | | 336 |
| 5 | 0.3 | | 1080 |
| 5 | 0.1 | 0.25 | 1512 |
| 6 | 0.1 | | 312 |
| 6 | 0.3 | | 1008 |
| 6 | 0.1 | 0.25 | 1344 |
| 7 | 0.1 | | 528 |
| 7 | 0.3 | | 1368 |
| 7 | 0.1 | 0.25 | 1584 |

EXAMPLE 8

(Preparation of calix [n] arene)

About 0.066 mole (10.0 g) p-tert-butylphenol, 0.133 mole (4.0 g) para-formaldehyde, and 6.0 ml. 5N RbOH were combined with 100 ml. xylene in a 500 ml. flask equipped with a Dean-Stark collector. The slurry was refluxed in an inert atmosphere overnight.

The cooled solution was filtered and the solids suspended in 300 ml. chloroform before washing with 100 ml. 10% HCl and then 100 ml. water. The organics were dried over $Na_2SO_4$ and concentrated to about 60 ml. A 10 ml. portion of ethanol was added to the slurry. The solids were collected (13.0 g) and placed under vacuum overnight at 75° C.

The product was analyzed and proved to be a 65:35 mixture of calix [6] arene to calix [4] arene.

Another calix [n] arene may be prepared in accordance with the procedure of Gutsche, Journal of the American Chemical Society, 1981, 103, 3782-3792.

The calix arenes have the structure:

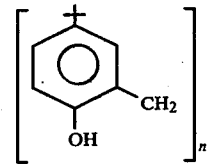

EXAMPLE 9

About 5.0 g of the cream colored product from Example 8 was combined with 50 ml. dry THF and 0.25 g 98% NaH under a nitrogen atmosphere. The mixture was heated to reflux for five hours. A 0.4 ml. portion of PCl₃ was added dropwise and the mixture refluxed overnight.

The cooled reaction mixture was poured over 75 ml. chloroform and washed with 100 ml. water. The organics were dried over Na₂SO₄ and concentrated to 5.0 g cream colored product under vacuum. The analysis is given in Table 2.

EXAMPLES 10-12

The same procedure was followed as for Example 1, but using large phenolics that form oligomers with PCl₃ rather than monomers or small ring phosphites such as is done with pentaerythritol or compounds having the diphenolic structure:

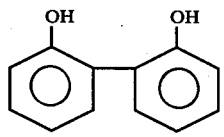

The compounds used were the following: tetrakis (methylene-3-[3',5'-di-tert-butyl-4'-hydroxyphenyl]propionate) methane (Example 10, compound II); 2,4,6-tris(3,5-di-tert-butyl-4-hydroxybenzyl) phenol (Example 11, compound III); and the o-tert-butylphenol/formaldehyde reaction product reacted with formaldehyde and a mixture of 2,6-di-tert-butylphenol, 4,4'-methylenebis(2,6-di-tert-butylphenol) and 3,5-di-tert-butyl-4-hydroxybenzyl alcohol, such mixture being the heel from production of the 3,5-di-tert-butyl-4-hydroxybenzyl alcohol (Example 12). The compounds are marketed as Ciba Geigy's Irganox®1010 antioxidant, Shell's Ionox®312 antioxidant, and Ethyl Corporation's Ethanox®738, respectively.

EXAMPLE 10
white solid

EXAMPLE 11
yellow solid

EXAMPLE 12
yellow solid

The adducts were analyzed as reported in Table 2.

Polypropylene plaques of 60 mil thickness were prepared according to the formulation given below and oven aged at 150° C. Norchem's Profax-6501 ™ polypropylene was used for the tests reported in Table 4.

TABLE 4

| | Polypropylene Oven Aging at 150° C. | | |
|---|---|---|---|
| Example | Wt. % Adduct | DSTDP | Hours to Fail |
| 9 | 0.1 | — | 120 |
| | 0.1 | 0.23 | 744 |
| 10 | 0.1 | — | 816 |
| 11 | 0.1 | — | 168 |
| | 0.1 | 0.25 | 792 |
| 12 | 0.1 | — | 408 |
| | 0.1 | 0.25 | 1032 |

For comparison, compound II protected polypropylene plaques. with and without 0.25 wt. % DSTDP failed at 2064 and 480 hours. Other substrates and conditions may produce varying results.

EXAMPLE 13

An adduct of the invention was compared to compound I for controlling discoloration caused by a synergist, in this case DSTDP, in polypropylene. Yellowness Index (YI) was compared on a Hunter Colorimeter after oven aging at 90° C. Plaques of 60 mil thick Profax ™ 6501 polypropylene were used for the comparison. Unsynergized plaques with compound I or the inventive adduct thereof showed little or no discoloration (YI=0-3) whereas the synergized plaque for compound I had a YI=41.0. The synergized plaques with the adducts of Examples 2, 1A and 5 had YI=22.0, 23.5, and 40.0 respectively.

It is possible to vary the organic substrate of the invention, the method of incorporating the adduct and/or some other features of the invention without departing from the scope or spirit thereof as defined by the appended claims.

I claim:

1. Organic material normally susceptible to gradual oxidative degradation, containing an antioxidant amount of an adduct formed by reacting at least about 0.05 mole parts of a phosphorus trihalide of formula PX₃ where the X are halides with one mole part of a large phenolic compound having four or more phenolic moieties, said phenolic compound being a calix (n) arene where n=4 to 10.

2. The composition of claim 1 wherein n=6.

3. The composition of claim 1 wherein the calix (n) arene is formed from p-tert-butylphenol.

4. The adduct formed by reacting at least about 0.05 mole parts of a phosphorus trihalide of formula PX₃ where the X are halides with one mole part of a calix (n) arene where n=4 to 10.

5. The adduct of claim 4 wherein n=4.

6. The adduct of claim 4 wherein n=6.

* * * * *